(12) United States Patent
Berckmans

(10) Patent No.: US 11,576,354 B2
(45) Date of Patent: Feb. 14, 2023

(54) METHOD FOR CUSTOMIZED MONITORING OF SOUNDS CAUSED BY RESPIRATORY DISTRESS

(71) Applicant: SOUNDTALKS NV, Heverlee (BE)

(72) Inventor: Dries Berckmans, Heverlee (BE)

(73) Assignee: SOUNDTALKS NV, Heverlee (BE)

( * ) Notice: Subject to any disclaimer, the term of this patent is extended or adjusted under 35 U.S.C. 154(b) by 938 days.

(21) Appl. No.: 16/348,424

(22) PCT Filed: Nov. 12, 2017

(86) PCT No.: PCT/EP2017/078973
§ 371 (c)(1),
(2) Date: May 8, 2019

(87) PCT Pub. No.: WO2018/091383
PCT Pub. Date: May 24, 2018

(65) Prior Publication Data
US 2019/0327938 A1    Oct. 31, 2019

(30) Foreign Application Priority Data

Nov. 15, 2016   (EP) .................................. 16002422

(51) Int. Cl.
*A61B 7/00*   (2006.01)
*A01K 29/00*  (2006.01)
(Continued)

(52) U.S. Cl.
CPC .......... *A01K 29/005* (2013.01); *A61B 5/0823* (2013.01); *A61B 7/003* (2013.01);
(Continued)

(58) Field of Classification Search
CPC ........ A01K 29/00; A01K 29/005; A61B 5/08; A61B 5/0823; A61B 7/00; A61B 7/003;
(Continued)

(56) References Cited

U.S. PATENT DOCUMENTS 7,761,302 B2    7/2010  Woodcock et al.
10,064,580 B2 *  9/2018  Brattain ................. A61B 7/003
(Continued)

FOREIGN PATENT DOCUMENTS

CN    105513613 A    4/2016
EP    2 783 629 A1   1/2014
(Continued)

OTHER PUBLICATIONS

D. Berckmans, "Automatic On-Line Monitoring of Animals by Precision Livestock Farming", originally published in International Society for Animal Hygiène—Saint-Malo, pp. 27-30, (2004), and republished as a chapter in "Livestock Production and Society", editors R. Greer and F. Madec, eISBN: 978-90-8686-567-3 | ISBN: 978-90-76998-89-3, pp. 51-54, (Jan. 2006).
(Continued)

*Primary Examiner* — David J. McCrosky
(74) *Attorney, Agent, or Firm* — The Marbury Law Group, PLLC

(57) ABSTRACT

The invention relates to a method for customized monitoring of sounds caused by respiratory distress in a group of farm animals in a specific farm, stable, or section of a stable, a non-transitory processor readable medium having stored thereon processor executable instructions configured to cause a processor to perform the method according to the invention, a computing device to carry out the method according to the invention, and a kit of parts for carrying out each of the inventive method comprising such a computing device and at least one microphone.

29 Claims, 4 Drawing Sheets

(51) Int. Cl.
     A61B 5/00    (2006.01)
     G16H 50/30   (2018.01)
     A61B 5/08    (2006.01)
     G16H 40/67   (2018.01)

(52) U.S. Cl.
     CPC ............ *G16H 50/30* (2018.01); *A61B 5/7267* (2013.01); *A61B 2503/40* (2013.01); *A61B 2562/0204* (2013.01); *G16H 40/67* (2018.01)

(58) Field of Classification Search
     CPC ..... A61B 7/04; A61B 5/7267; A61B 2503/40; A61B 2562/0204; A61B 5/7264; A61B 5/7275; G16H 50/30
     See application file for complete search history.

(56) References Cited

U.S. PATENT DOCUMENTS

| | | | |
|---|---|---|---|
| 11,389,080 B2* | 7/2022 | Geissler | A61B 7/003 |
| 2002/0010390 A1 | 1/2002 | Guice et al. | |
| 2013/0150744 A1 | 6/2013 | Brattain et al. | |
| 2020/0022337 A1 | 1/2020 | Genzow et al. | |

FOREIGN PATENT DOCUMENTS

| | | |
|---|---|---|
| JP | 2011-217934 A | 11/2011 |
| WO | 2008/152433 A1 | 12/2008 |
| WO | 2008/154662 A1 | 12/2008 |
| WO | 2014/118788 A2 | 8/2014 |
| WO | 2014/123732 A1 | 8/2014 |
| WO | 2015/083153 A2 | 6/2015 |

OTHER PUBLICATIONS

Genzow, et al., "Monitoring of a commerical fattening herd by means of the Pig Cough Monitor and oral fluid diagnostics", (1 page version attached), published originally in Proceedings of the 23rd IPVS Congress, Cancun, Mexico (2014), pp. 205-206.

International Search Report and Written Opinion of the International Searching Authority received from the European Patent Office in International Application No. PCT/EP2017/078973 dated Feb. 2, 2018.

Ferrari, et al., "Cough sound analysis to identify respiratory infection in pigs", www.sciencedirect.com, Computers and Electronics in Agriculture vol. 64, No. 2, pp. 318-325, (Dec. 1, 2008).

Ferrari, et al., "Cough sound description in relation to respiratory diseases in dairy calves", www.elsevier.com/locate/prevetmed, Preventive Veterinary Medicine 96, pp. 276-280, (2010).

Hirtum, "The acoustics of coughing", Katholieke Universiteit Leuven, Faculty of Applied and Biological Engineering, Leuven, Belgium, Medical Physics, vol. 29, No. 12, p. 2965, (Dec. 2002).

Hirtum, et al., "Objective Cough-Sounds Recognition as a Biomarker for Aerial Factors", Transactions of the ASAE, vol. 47(1), 2004 American Society of Agriculture Engineers ISSN 0001-2351, pp. 351-356, (2004).

Hirtum, et al., "Fuzzy approach for improved recognition of citric acid induced piglet coughing from continuous registration", www.sciencedirect.com, Journal of Sound and Vibration 266, pp. 677-686, (2003).

Moura, et al., "Noise Analysis to Evaluate Chick Thermal Comfort", Sci. Agric. (Piracicaba, Braz.), v.65, n.4, pp. 438-443, (Jul./Aug. 2008).

Aydin, et al., "A novel method to automatically measure the feed intake of broiler chicken by sounds technology", www.elsevier.com/locate/compag, Computers and Electronics in Agriculture 101, pp. 17-23, (2014).

Hillman, et al., Vocalisation of domestic pigs (*Sus scrofa domestica*) as an indicator for their adaptation towards ambient temperatures, www.sciencedirect.com, Applied Animal Behaviour Science 89, pp. 195-206, (2004).

Finger, et al., "Practical application of the Pig Cough Monitor in a German fattening pig herd with PRDC", published in Proceedings of the 23rd IPVS Congress, Cancun, Mexico (2014), pp. 207-208.

Genzow, et al., "Course of cough in two batches of fattening pigs with different respiratory pathogen exposure", published in Proceedings of the 23rd IPVS Congress, Cancun, Mexico (2014), pp. 212-213.

Berckmans, et al., "Animal Sound . . . Talks! Real-time Sound Analysis for Health Monitoring in Livestock", Int. Symp. on Animal Environ. & Welfare, Chongqing, China, pp. 215-222, (Oct. 23-26, 2015).

Hirtum, et al., "Assessing the sound of cough towards vocality", Medical Engineering & Physics 24, pp. 535-540, (2002).

Kimman et al., "Banning Antibiotics, Reducing Resistance, Preventing and Fighting Infections" White Paper on Research Enabling an 'Antibiotic-free' Animal Husbandry, Wageningen Academic UR, 74 pgs.

Aarestrup, "Get Pigs off Antibiotics", vol. 486, Nature, pp. 465-466, (Jun. 28, 2012).

Genzow, et al., "Monitoring of a commercial fattening herd by means of the Pig Cough Monitor and oral fluid diagnostics", Proceedings of the 23rd IPVS Congress, Cancun, Mexico (2014), 1 page.

* cited by examiner

METHOD FOR CUSTOMIZED MONITORING OF SOUNDS CAUSED BY RESPIRATORY DISTRESS

CROSS-REFERENCE TO RELATED APPLICATIONS

This application claims priority to, and is the 35 U.S.C. § 371 U.S. National Phase of, Patent Cooperation Treaty application no. PCT/EP2017/078973 filed on Nov. 12, 2017 which claims the benefit from the priority of European patent application EP 16002422.0 filed on Nov. 15, 2016; the entire contents of both of these applications are hereby incorporated by reference.

BACKGROUND OF THE INVENTION

1. Technical Field

The invention relates to a method carried out by a processor for customized monitoring of sounds caused by respiratory distress in a group of farm animals in a specific farm, stable, or section of a stable, a non-transitory processor readable medium having stored thereon processor executable instructions configured to cause a processor to perform the method according to the invention, a computing device to carry out the method according to the invention, and a kit of parts for carrying out he inventive method comprising such a computing device and at least one microphone.

2. Background Information

In recent years, several factors have stressed traditional livestock farming. Firstly, the global meat demand has grown extremely as the world population continues to grow. Furthermore, income per capita is increasing, particularly in the upcoming industries like the BRIC-countries. This enables massive new groups of people to consume meat. Another trend specific to consumers in developed countries is the augmented concern towards ethical and environmentally friendly meat production. Additionally, there is a clear need for a reduction in the use of antibiotics in intensive livestock production (Aarestrup, F. 2012, Nature 486, 465-466; Kimman, T., Smits, M., Kemp, B., Wever, P., and Verheijden, J. 2010. Banning Antibiotics, Reducing Resistance, Preventing and Fighting Infections: White Paper on Research Enabling an Antibiotic-free' Animal Husbandry. Wageningen Academic UR).

Livestock farming may be regarded as a process control technology, in which context the term Precision Livestock Farming (PLF) is often used (Berckmans, D. 2006, in Livestock Production and Society, R. Geers, and F. Madec, eds. Wageningen Academic Publishers. 51-54). PLF is based on three guiding principles. Firstly, PLF does not aim to replace the farmer but intends to be a decision support tool. Secondly, the animal is to be considered the most crucial part in the biological production process. Lastly, three conditions are important for favourable monitoring and control: the animal variables need to be monitored, the prediction (expectation) of the animal variable should be reliable with respect to environmental changes and the prediction needs to be integrated with on-line measurements into an analysing algorithm.

Different kinds of sensors are employed to facilitate PLF in a practical setup, e.g., cameras (CCTV, infra-red, 3D, thermal . . . ), accelerometers, flow meters, etc. A particularly interesting type of PLF techniques uses microphones to capture sound. Sound contains a lot of useful information about the animal and its environment (communication, health, welfare . . . ).

Recently, a number of examples of sound-based PLF-technology have emerged in different species. Moura et al. showed how thermal (dis-) comfort can be monitored in broilers based on sound analysis (Moura, D. J. de, Nääs, I. de A., Alves, E. C. de S., Carvalho, T. M. R. de, do Vale, M. M., and Lima, K. A. O. de 2008, Sci. Agric. 65, 438-443), while Aydin et al. demonstrated the monitoring of broiler feed intake by pecking sounds (Aydin, A., Bahr, C., Viazzi, S., Exadaktylos, V., Buyse, J., and Berckmans, D. 2014. Comput. Electron. Agric. 101, 17-23). Hillman et al. used acoustic monitoring of pigs for the detection of thermal (dis-) comfort (Hillmann, E., Mayer, C., Schön, P.-C., Puppe, B., and Schrader, L. 2004, Appl. Anim. Behav. Sci. 89, 195-206).

Van Hirtum et al. first developed algorithms to discriminate pathological from non-pathological pig coughs (Van Hirtum, A. 2002. The acoustics of coughing. PhD Thesis. KU Leuven. Leuven, Belgium). Ferrari et al. did a characterisation of pig cough sounds using time and frequency-derived parameters (Ferrari et al., 2008).

The link between automatically measured cough and in respiratory porcine health has been validated extensively in several field trials (Finger, G., Hemeryck, M., Gomez-Duran, O., and Genzow, M. 2014, in *Proceedings of the 23rd IPVS Congress*, Cancun, Mexico. 207-208; Genzow, M., Gomez-Duran, O., Hemeryck, M., and Finger, G. 2014a, in *Proceedings of the 23rd IPVS Congress*, Cancun, Mexico. 212-213; Genzow, M., Gomez-Duran, O., Strutzberg-Minder, K., Finger, G., and Hemeryck, M. 2014b, in *Proceedings of the 23rd IPVS Congress*, Cancun, Mexico. 205-206; Berckmans, D., Hemeryck, M., Berckmans, D., Vranken, E., van Waterschoot, T., 2015 in *Int. Symp. on Animal Environ. &Welfare, Oct. 23-26, 2015, Chongqing, China*).

The International patent application WO 2008/154662 teaches a method and/or system for combining the respiratory status (e.g. amount and type of cough) with the localization of organisms having the respiratory status in real time.

The International patent application WO 2014/118788 suggest a method and/or a system for monitoring a population of livestock with the aid of one or more optical sensors and a processor configured for assessing changes of behavior.

However, the methods described hitherto did not take into account that the environments of individual farms, stables or parts thereof differ from each other and that the environment may change over the time. Accordingly, there is a high demand for a customized measurement of sounds caused by respiratory distress in the individual environment, which is time and location specific. The problem underlying the present invention was to provide a customized early warning method based on sounds caused by respiratory distress in a specific environment at a specific moment in time.

This problem has been solved by a method wherein the respiratory distress index (RDI) being the number of sounds caused by respiratory distress within a pre-defined period of time is measured, monitored and stored over a period of time and the time-specific individual relevant threshold for the RDI of the specific farm, stable or section thereof is calculated; wherein the calculation of the actual relevant threshold for the RDI is carried out by statistical process control.

The respiratory distress index (RDI) can optionally be scaled with the number of farm animals in the vicinity of the microphone.

BRIEF SUMMARY OF THE INVENTION

Accordingly, the invention relates to a method for customized monitoring of sounds caused by respiratory distress in a group of farm animals in a specific farm, stable, or section of a stable, comprising the following steps:

a) recording the noises generated in the group of the farm animals over a certain period of time;

b) converting the analogue recording into digital data;

c) performing filtering operations, which filter off background noises from sounds caused by respiratory distress;

d) counting the number of sounds caused by respiratory distress during the recording time;

e) calculating the respiratory distress index (RDI) being the number of sounds caused by respiratory distress within a pre-defined period of time, optionally corrected for the number of farm animals within the reach of each microphone;

f) monitoring and storing the RDI over a period of time and calculating the time-specific individual relevant threshold for the RDI of the specific farm, stable or section of a stable;

g) reporting the resulting RDI data, in relation to the threshold calculated in step f), wherein the steps c) to g) are carried out by a processor, and the calculation of the actual relevant threshold for the RDI in step f) is carried out by statistical process control (SPC).

The invention further relates to a non-transitory processor readable medium having stored thereon processor executable instructions configured to cause one or more processors to perform each of the inventive method steps c) to h).

Furthermore, the invention relates to a computing device for customized monitoring of sounds caused by respiratory distress in a group of farm animals in a specific farm, stable, or section of a stable, wherein said computing device comprises means to carry out the method steps b) to h) according to the invention.

In addition, the invention relates to a kit of parts for carrying out each of the method steps according to the invention consisting essentially of (A) an inventive computing device;

(B) at least one microphone connectable with said computing device (A); and (C) optionally an information booklet providing instruction for the installation and utilization of (A) and (B).

BRIEF DESCRIPTION OF THE DRAWINGS

The accompanying drawings illustrate embodiments of the invention, and, together with specification, including the general description above and the detailed description, which follows, serve to explain the features of the present invention.

FIG. 3 (a) Respiratory Distress Sounds counted per recording period;

FIG. 3 (b) Respiratory Distress index over aggregated time period;

FIG. 3 (c) Factor between newly aggregated RDI and previous aggregated RDI aggregated, relative to the standard deviation of the RDI Aggregated over longer time frame, FIG. 3 (d) Evolution of RDI over aggregated period and upper and lower acceptable thresholds (time-specific, individual).

DETAILED DESCRIPTION OF THE INVENTION

Figure 1:
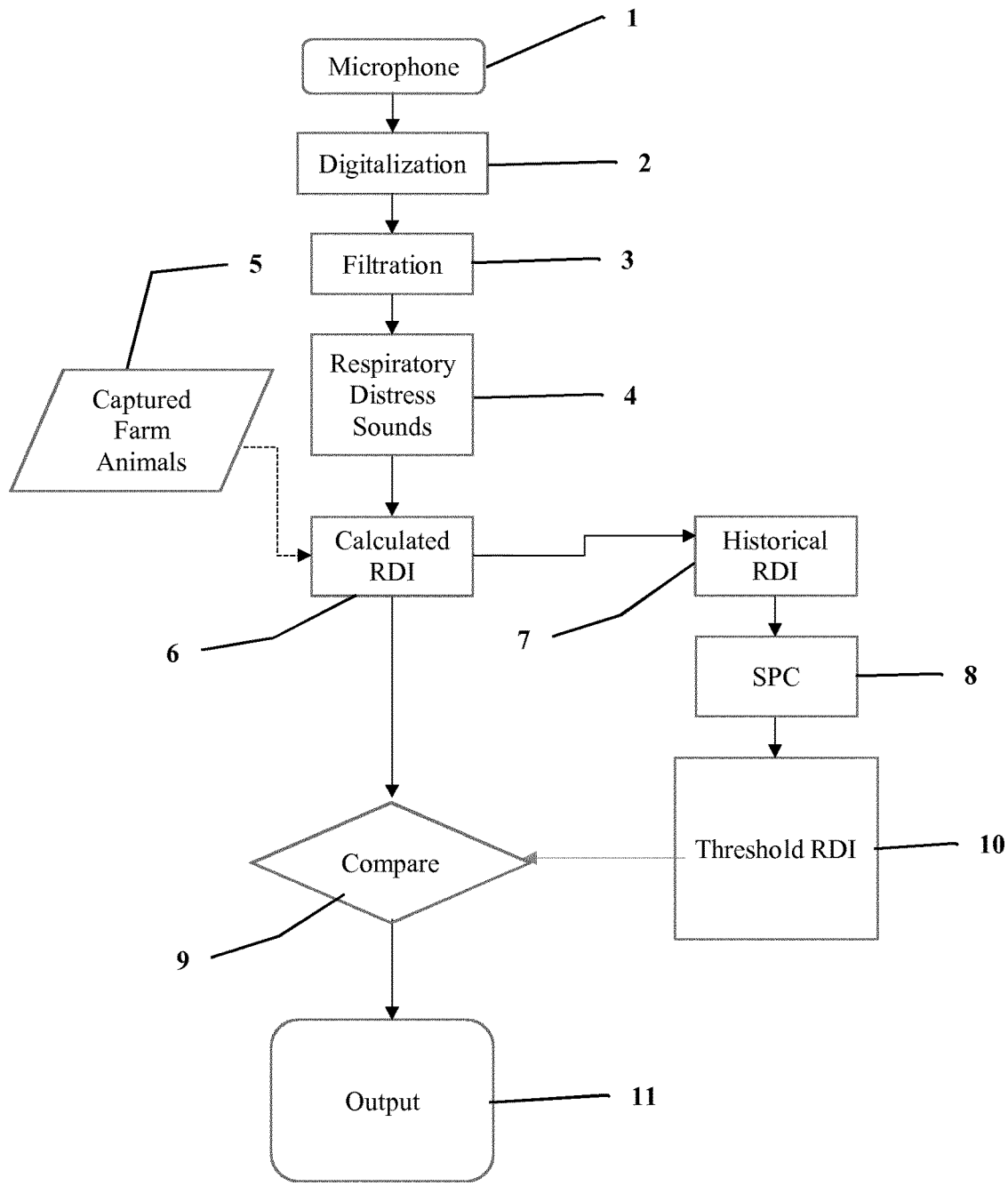
FIG. 1 is a process flow diagram illustrating an embodiment of the method according to the invention.

The term "customized monitoring" as used hereinabove or hereinbelow means that the monitoring is specific for the actual farm, stable or part of a stable. Each farm, stable or part of a stable has its typical sounds and noises depending on the site, the environment, the animals, the ventilation, the machines used or the farmers, which also changes with time. The method according to the invention utilizes statistical process control (SPC) in order to adapt monitoring over time to the specific farm, stable or part of a stable.

The term "sounds of respiratory distress" as used hereinabove or hereinbelow includes all kinds of sounds that farm animals make due to respiratory disorders or diseases including but not limited to coughing, sneezing, harrumphing and wheezing.

The term "farm animals" as used hereinabove or hereinbelow includes all kinds of animals which are maintained in a farm for production of animal product or for leisure, such as, horses, dogs, donkeys, ostriches and minks, in particular pigs, cattle and poultry, including turkeys, chickens, goose and ducks.

The term "processor" as used hereinabove or hereinbelow means a computing device such as an industrial computer, a personal computer (PC), laptop, or tablet, which may be located within the farm, stable, or section of a stable, or is connected via data transfer means with a microphone located within the farm, stable, or section of a stable.

The term "connected" or "connectable" used hereinabove or herein below with respect to the relationship of the microphone and the computing device is intended to include any direct linkage by a suitable cable or wire, but also any wireless connection such as infrared, Bluetooth® or WLAN.

The term "computing device" as used hereinabove and hereinbelow means not only a processor in a housing connected to the microphone, but also includes a system comprising a device that first receives the raw or processed acoustic data from the microphone, then stores such data in a processor readable medium and later transmits it to a processor.

The term "processor readable medium" as used hereinbefore or hereinbelow includes any medium that can be used to store digital data including but not limited to internal or external hard drives, SSD drives, SDI cards, storage clouds, CDs, DVDs, USB sticks, floppy discs and magnetic tapes.

The following methods are preferred embodiments of the present invention:

A method, wherein (i) the method is used as an early warning system;

(ii) the RDI in step e) is corrected for the number of farm animals within the reach of each microphone;

(iii) the farm animals are selected from the group consisting of cattle, pigs, horses and poultry, in particular fattening pigs;

(iv) the sound caused by respiratory distress is sneezing and/or coughing;

(v) the noises generated in the group of the farm animals are recorded over a period of at least two weeks;
(vi) in step a) the noises produced by 1 to 1000 farm animals are recorded using 1 to 4 microphones, depending on the size of the monitored farm animals, in preferably 5 to 200 pigs, 10 to 1000 chicken, or 1 to 50 cows.
(vii) in step e) the RDI is the number of sounds caused by respiratory distress per single farm animal within 1 to 48 hours, preferably 12 to 36 hours, in particular within 24 hours, in another preferred embodiment during hours of low activity in the farm such as the night time.
(viii) in step f) the individual relevant threshold for the RDI of the specific farm, stable or section of a stable at a certain moment in time is automatically calculated by a processor using SPC based on the historical RDI data of the same specific farm, stable or section of a stable. The factor between the deviation and the expected deviation form the basis of the individual relevant threshold for the RDI of the specific farm. By way of non-limiting example, a formula which may be used to determine this factor is given by:

$$F\_x+N+2 = \frac{|(RDI\_AGG\_x+N+1 - RDI\_AGG\_x+N+2)|}{\sigma(RDI\_AGG\_X+N+1)}$$

wherein
F_x+N+2 is the time dependent and individual factor
RDI_AGG_x+N+1 is the penultimate aggregated RDI value
RDI_AGG_x+N+2 is the latest aggregated RDI value
σ (RDI_AGG_X+N+1) is the standard deviation of the series of aggregated RDI values preceding the latest aggregated RDI value.
(ix) in step h), the processor produces a report, preferably on the screen of a computing device or in printed form, indicating one or more RDI values (potentially in aggregated form), in combination with the relevant threshold RDI values and/or transmits such report to the user, preferably the stockman or veterinary health professional, who is in charge of the group of farm animals.

The various embodiments will be described in detail with reference to the accompanying drawings. Where possible the same reference numbers will be used throughout the drawings to refer to the same or like parts. References made to particular examples and implementations are for illustrative purposes, and are not intended to limit the scope of the claims.

The process flow diagram of FIG. 1 shows how one or more microphones (1) first pick up the sounds that occur in a farm, stable or part of the stable. The sounds are then converted from an analogue to a digital signal by an analogue-to-digital convertor (2). After digitalization, different filtering techniques (3) are applied to separate respiratory distress sounds from all other sounds that are captured by the microphone(s). The other sounds include both stationary background sounds like e.g. fan noise or feeding line noise, and transient sound events that are not related to respiratory distress, such as e.g. knocks or screams. The respiratory distress index (RDI) (6) is then calculated as the number of sounds (4) caused by respiratory distress within a predefined period of time, optionally scaled with the number of captured farm animals (5), i.e. those in the vicinity of the microphone(s) (1) as shown in FIG. 4A. The RDI values are stored over a period of time and a series of historical RDI values (7) serves as input for the calculation of the time-specific individual relevant threshold for the RDI of the specific farm, stable or section of a stable. The calculation of the time-specific individual relevant threshold (10) occurs by applying statistical process control (SPC) techniques (8) on series of aggregated historical RDI values (7). The actual calculated aggregated RDI (6) value is then compared with the time and location specific thresholds of the aggregated RDI (10). This comparison (9) serves as the output of the method (11), reporting the resulting RDI data compared to the relevant threshold.

Figure 2:
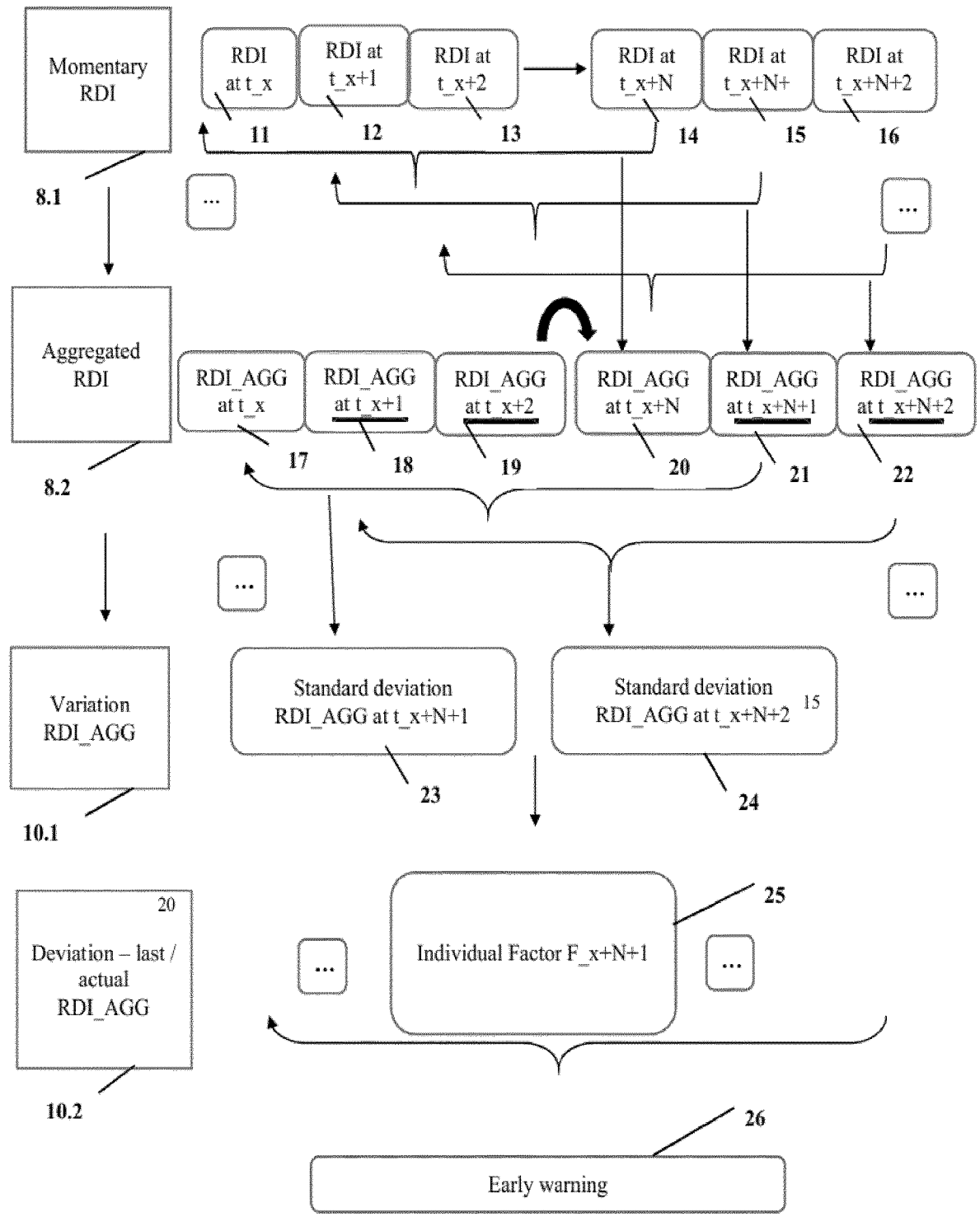
FIG. 2 is a detailed process flow diagram illustrating another embodiment.

The process flow diagram of FIG. 2 shows in more detail the process of applying statistical process control (SPC) techniques (8) on historical (aggregated) RDI values (8.1) for the calculation of time-specific individual relevant thresholds. First, momentary RDI values (RDI at t_x, through RDI at t_x+N+2) (11, 12, 13, 14, 15, 16) are calculated per short time interval (e.g. 5 to 60 minutes, see also the example in FIG. 3A). In the next step, RDI-values are aggregated over longer time intervals (8.2) (e.g. per 1 to 150 hours, see also FIG. 3B) (17, 18, 19, 20, 21, 22) to obtain a curve with more predictable behaviour, i.e. a curve with RDI_AGG values. A series of historical RDI_AGG values (e.g. a series of 1 to 500 days) is then used to apply statistical process control. In the next step, the variation in the series of historical RDI_AGG values (10.1) is calculated via the standard deviation of the series of historical RDI_AGG data at t_x+N+1 (23) and the standard deviation of the series of historical RDI_AGG data at t_x+N+2 (24). Next, the deviation (10.2) between the last RDI_AGG-value and the actual RDI_AGG-value is expressed relative to the expected variation in the historical RDI_AGG series. The expected variation is determined based on the standard deviation in the series of historical RDI_AGG values. The time dependent and individual factor F_x+N+1 is calculated by dividing the difference between the latest RDI_AGG value and the previous RDI_AGG value by the standard deviation of the series of historical RDI_AGG data (25). The factor between the deviation and the expected deviation is shown in FIG. 3C. Based on this factor, early warning is defined (26) as shown in FIG. 3D.

Figure 3:
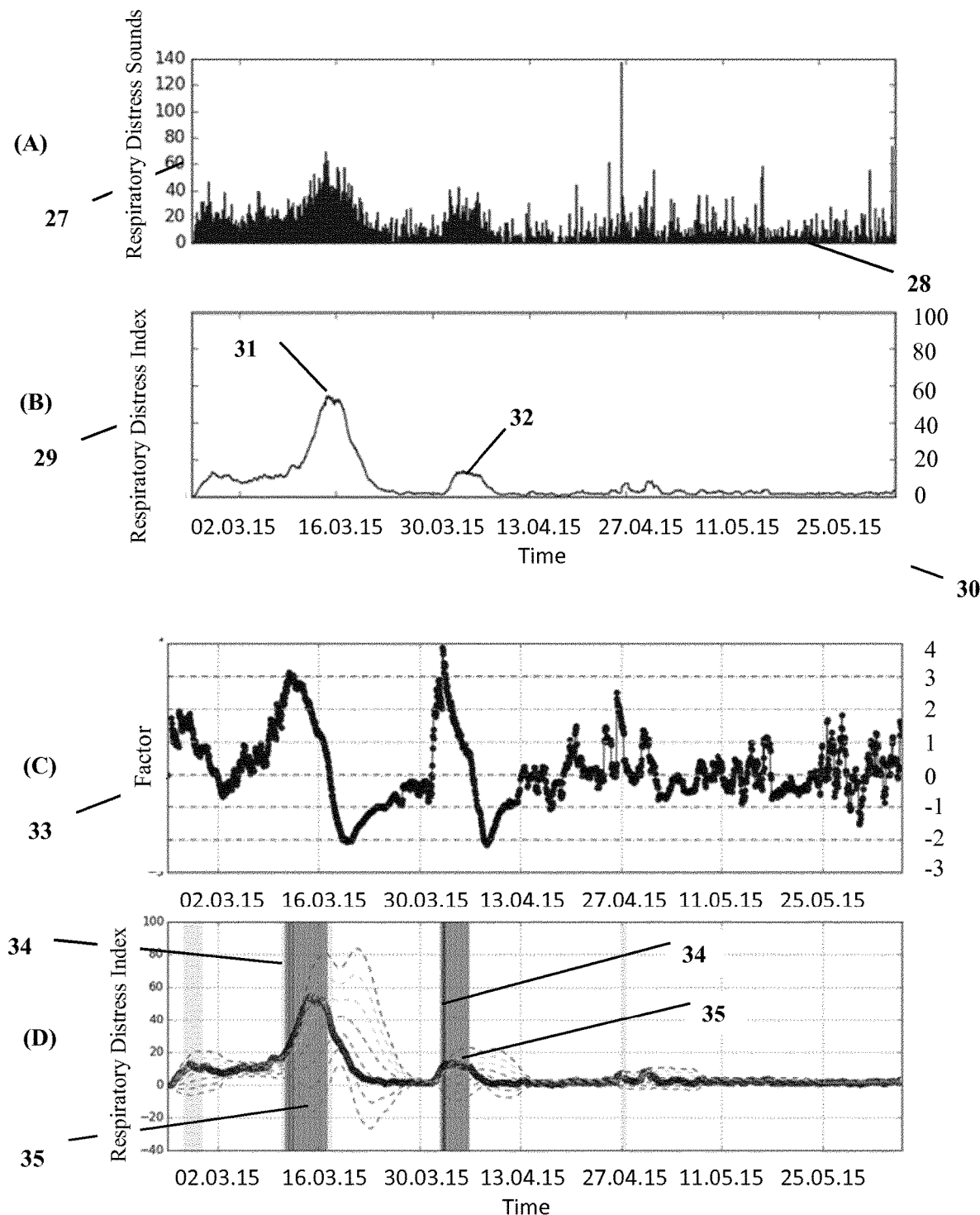
FIG. 3 illustrates the resulting output data of RDI values monitoring a specific stable according to the invention.

FIG. 3 shows an example of the proposed method. FIG. 3A first shows the number of respiratory distress sounds as the ordinate (27) per short time interval (5 minutes here) as the X-axis (28). FIG. 3B shows how, from these RDI-values, the aggregated RDI-AGG values (29) in function of time (30) are calculated by aggregating the data over a longer time interval. In this example, it is clear that there is an increase in RDI-AGG values around Mar. 16, 2015 (31) and a second (smaller) increase in the beginning of April 2015 (32). The standard deviation of a series of RDI-AGG values in FIG. 3B are then used to determine the expected variation in the data. FIG. 3C then shows the resulting factor (33) in function of time, i.e. the difference between the last RDI_AGG and the previous RDI_AGG, relative to the standard deviation of the preceding series of RDI-AGG values. The evolution of this factor over time is then used to define early warnings, in this example there is a dark warning bar (34) when the factor is higher than 3 and a lighter bar (35) warning when the factor is between 2 and 3 as can be seen in FIG. 3D.

Figure 4:
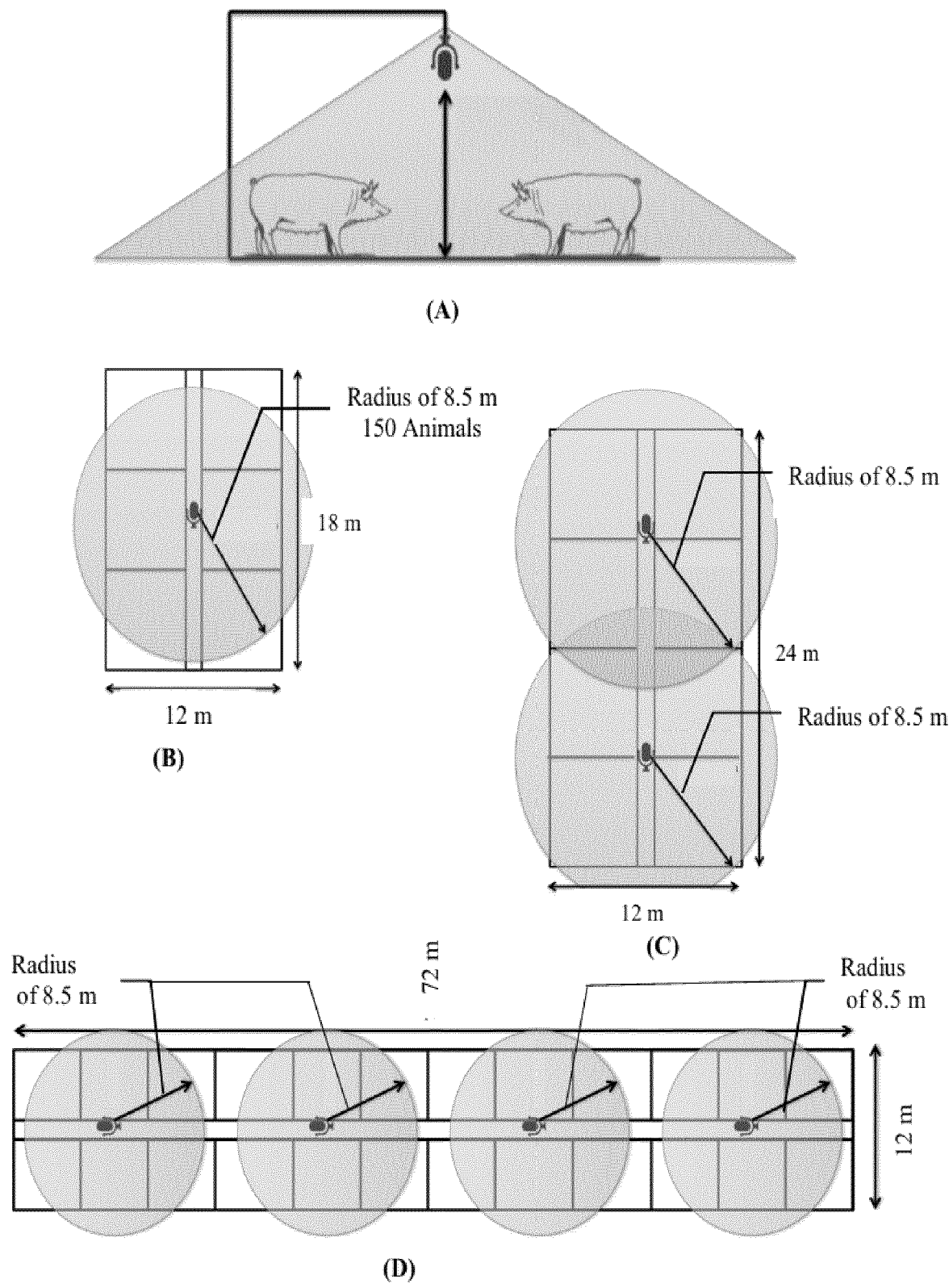
FIG. 4 illustrates different exemplary arrangements of the sound monitoring system in farm stables.

FIG. 4 illustrates different exemplary arrangements of the sound monitoring system in farm stables.

FIG. 4A shows a schematic cross-section of a pig stable, in which the microphone is mounted at the ceiling of the stable at a height of about 2 meters. The sounds made by all animals within a radius of about 7 to 9 meters on the ground are within the reach of the microphone.

FIG. 4B shows a top view of six pigpens with a length of about 6 meters and a width of about 5 meters. The total pig population is 225. One microphone records the sounds made by about 75% of the animals.

FIG. 4C shows a top view of eight pigpens with a length of about 6 meters and a width of about 5 meters. The total pig population is 320. Two microphones record the sounds made by all the animals.

FIG. 4D shows a top view of twenty-four pigpens with a length of about 6 meters and a width of about 5 meters. The total pig population is 1000. Four microphones record the sounds made by about 75% of the animals.

The preceding description of the disclosed embodiments is provided to enable a person skilled in the art to make or use the present invention. Various modifications of these embodiments will be readily apparent to those skilled in the art, and the general principles defined herein may be applied to other embodiments without departing from the spirit or scope of the invention. Thus, the present invention is not intended to be limited to the embodiments shown herein but to be accorded the widest scope consistent with the following claims and the principles and features disclosed herein.

The invention claimed is:

1. A method for customized monitoring of sounds caused by respiratory distress in a group of farm animals in a specific farm, stable, or section of a stable, the method comprising the following steps:
   a) recording noises generated in the group of farm animals in one or more pens of the specific farm, stable, or section of a stable over a recording time as an analogue recording using a selected number of microphones positioned in the specific farm, stable or section of a stable relative to the one or more pens such that the selected number of microphones records noises from about seventy-five percent or greater of the group of farm animals;
   b) converting the analogue recording into digital data;
   c) performing filtering operations on the digital data by a processor, wherein the filtering operations filter off background noises from sounds caused by respiratory distress;
   d) counting, by the processor, a number of sounds caused by respiratory distress during the recording time;
   e) calculating, by the processor, a latest aggregated respiratory distress index (RDI) based at least in part on a number of sounds caused by respiratory distress within a pre-defined period of time within the recording time;
   f) comparing, by the processor, the latest aggregated RDI to a time-specific individual relevant threshold for a RDI of the specific farm, stable, or section of a stable, wherein the time-specific individual relevant threshold for the RDI of the specific farm, stable, or section of a stable is determined by statistical process control (SPC); and
   g) reporting, by the processor, the result of the comparison of the latest aggregated RDI data to the time-specific individual relevant threshold for the RDI of the specific farm, stable, or section of a stable.

2. The method of claim 1, wherein the latest aggregated RDI is corrected for a number of animals within reach of the selected number of microphones used to recording the noises generated in the group of farm animals.

3. The method of claim 1, wherein the group of farm animals are selected from the group consisting of cattle, pigs, horses and poultry and the one or more pens are each six meter length by five meter width pens.

4. The method of claim 1, wherein the group of farm animals are fattening pigs.

5. The method claim 1, wherein the sounds caused by respiratory distress are sneezing or coughing.

6. The method claim 1, wherein the recording time is a period of at least 2 weeks.

7. The method of claim 1, wherein:
the one or more pens is six to twenty-four pens;
the group of farm animals is 1 to 1000 farm animals; and
the selected number of microphones is 1 to 4 microphones.

8. The method of claim 1, wherein:
the pre-defined period of time is 24 hours; and
the latest aggregated RDI is further based at least in part on a number of sounds caused by respiratory distress per single farm animal within the pre-defined period of time within the recording time.

9. The method of claim 1, wherein recording the noises in step a) is performed during hours of reduced activity.

10. The method of claim 1, further comprising automatically determining, by the processor, the time-specific individual relevant threshold for the RDI of the specific farm, stable, or section of a using SPC based on previous RDI data of the specific farm, stable, or section of a stable.

11. The method of claim 1, wherein the time-specific individual relevant threshold for the RDI of the specific farm, stable, or section of a stable is based at least in part on a factor between a deviation based at least in part on the latest aggregated RDI and an expected deviation based at least in part on historical aggregated RDIs of the specific farm, stable, or section of a stable.

12. The method of claim 1, wherein the time-specific individual relevant threshold for the RDI of the specific farm, stable, or section of a stable is determined by the formula:

$$F\_x+N+2 = \frac{|(RDI\_AGG\_x+N+1 - RDI\_AGG\_x+N+2)|}{\sigma(RDI\_AGG\_X+N+1)}$$

wherein:
F_x+N+2 is a time dependent and individual factor;
RDI_AGG_x+N+1 is a penultimate aggregated RDI value;
RDI_AGG_x+N+2 is the latest aggregated RDI; and
6 (RDI_AGG_X+N+1) is a standard deviation of a series of aggregated RDI values preceding the latest aggregated RDI.

13. The method of claim 12, wherein the latest aggregated RDI is corrected for a number of animals within reach of the selected number of microphones used to recording the noises generated in the group of the farm animals.

14. The method of claim 12, wherein the group of farm animals are selected from the group consisting of cattle, pigs, horses and poultry.

15. The method of claim 12, wherein the group of farm animals are fattening pigs.

16. The method of claim 12, wherein the sounds caused by respiratory distress are sneezing or coughing.

17. The method of claim 12, wherein the recording time is a period of at least 2 weeks.

18. The method of claim 12, wherein:
the one or more pens is six to twenty-four pens each having a length of six meters and a width of five meters;

the group of farm animals is 1 to 1000 farm animals; and
the selected number of microphones is 1 to 4 microphones each mounted in the specific farm, stable or section of a stable at a height of two meters.

19. The method of claim 12, wherein:
the pre-defined period of time is 24 hours; and
the latest aggregated RDI is further based at least in part on a number of sounds caused by respiratory distress per single farm animal within the pre-defined period of time within the recording time.

20. The method of claim 12, wherein recording the noises in step a) is performed during hours of reduced activity.

21. The method of claim 12, further comprising automatically determining, by the processor, the time-specific individual relevant threshold for the RDI of the specific farm, stable, or section of a stable using SPC based on previous RDI data of the specific farm, stable, or section of a stable.

22. The method of claim 12, wherein:
the report indicates one or more RDI values in combination with the time-specific individual relevant threshold for the RDI of the specific farm, stable, or section of a stable; and
step g) comprises displaying the report on a screen of a computing device to a user or generating a printed copy of the report.

23. The method of claim 1, wherein:
the report indicates one or more RDI values in combination with the time-specific individual relevant threshold for the RDI of the specific farm, stable, or section of a stable; and
step g) comprises displaying the report on a screen of a computing device to a user or generating a printed copy of the report.

24. A non-transitory processor readable medium having stored thereon processor executable instructions configured to cause a processor to perform operations comprising:
recording noises generated in a group of farm animals in one or more pens of a specific farm, stable, or section of a stable over a recording time as an analogue recording using a selected number of microphones positioned in the specific farm, stable or section of a stable relative to the one or more pens such that the selected number of microphones records noises from at least seventy-five percent of the group of farm animals;
converting the analogue recording into digital data;
performing filtering operations on the digital data, wherein the filtering operations filter off background noises from sounds caused by respiratory distress;
counting a number of sounds caused by respiratory distress during the recording time;
calculating a latest aggregated respiratory distress index (RDI) based at least in part on a number of sounds caused by respiratory distress within a pre-defined period of time within the recording time;
comparing the latest aggregated RDI to a time-specific individual relevant threshold for a RDI of the specific farm, stable, or section of a stable, wherein the time-specific individual relevant threshold for the RDI of the specific farm, stable, or section of a stable is determined by statistical process control (SPC); and
reporting the result of the comparison of the latest aggregated RDI data-to the time-specific individual relevant threshold for the RDI of the specific farm, stable, or section of a stable.

25. The non-transitory processor readable medium of claim 24, wherein the stored processor executable instructions are configured to cause a processor to perform operations such that the time-specific individual relevant threshold for the RDI of the specific farm, stable, or section of a stable is determined by the formula:

$$F\_x+N+2 = \frac{|(RDI\_AGG\_x+N+1 - RDI\_AGG\_x+N+2)|}{\sigma(RDI\_AGG\_X+N+1)}$$

wherein:
F_x+N+2 is a time dependent and individual factor;
RDI_AGG_x+N+1 is a penultimate aggregated RDI value;
RDI_AGG_x+N+2 is the latest aggregated RDI; and
σ(RDI_AGG_X+N+1) is a standard deviation of a series of aggregated RDI values preceding the latest aggregated RDI.

26. A system for customized monitoring of sounds caused by respiratory distress in a group of farm animals in a specific farm, stable, or section of a stable, comprising:
a selected number of microphones for mounting in the specific farm, stable, or section of a stable for recording noises from a group of animals in the specific farm, stable, or section of a stable;
a screen;
a drive; and
a processor coupled to the selected number of microphones, the screen, and the drive programmed with executable instructions including producing a latest aggregated respiratory distress index (RDI) report and indication of a time-specific individual relevant threshold for a RDI of the specific farm, stable, or section of a stable to the screen, wherein the latest aggregated RDI is based at least in part on a number of sounds caused by respiratory distress recorded using the selected number of microphones within a pre-defined period of time within a recording time, and wherein the time-specific individual relevant threshold for the RDI of the specific farm, stable, or section of a stable was determined by statistical process control (SPC).

27. The system of claim 26, wherein the latest aggregated RDI is corrected for a number of animals within reach of the selected number of microphones.

28. The system of claim 27, further comprising:
the specific farm, stable, or section of a stable having one or more pens therein;
wherein:
the selected number of microphones are arranged relative to the one or more pens such that the selected number of microphones records noises from about seventy-five percent or greater of the group of farm animals.

29. The system of claim 28, wherein:
the one or more pens is six to twenty-four pens each having a length of six meters and a width of five meters; and
the selected number of microphones is 1 to 4 microphones each mounted in the specific farm, stable or section of a stable at a height of two meters.

* * * * *